United States Patent
Kriesel et al.

(10) Patent No.: US 11,505,956 B1
(45) Date of Patent: Nov. 22, 2022

(54) STABILIZED HYGIENIC TRAYS

(71) Applicant: Universal Tech Corporation, Ettrick, WI (US)

(72) Inventors: Matthew Wayne Kriesel, Melrose, WI (US); Troy Bradley Goodenough, Mindoro, WI (US)

(73) Assignee: Universal Tech Corporation, Ettrick, WI (US)

( * ) Notice: Subject to any disclaimer, the term of this patent is extended or adjusted under 35 U.S.C. 154(b) by 980 days.

(21) Appl. No.: 15/932,829

(22) Filed: May 3, 2018

Related U.S. Application Data

(63) Continuation-in-part of application No. 15/731,815, filed on Aug. 7, 2017, now Pat. No. 11,124,596, which is a continuation-in-part of application No. 14/999,722, filed on Jun. 20, 2016, now Pat. No. 10,807,767.

(60) Provisional application No. 62/231,004, filed on Jun. 22, 2015.

(51) Int. Cl.
| | |
|---|---|
| *E04G 23/02* | (2006.01) |
| *G06K 15/02* | (2006.01) |
| *B32B 7/12* | (2006.01) |
| *A61B 50/33* | (2016.01) |
| *B65D 1/34* | (2006.01) |
| *B41J 2/01* | (2006.01) |
| *C08G 18/48* | (2006.01) |
| *C08G 18/10* | (2006.01) |
| *C08G 18/36* | (2006.01) |

(52) U.S. Cl.
CPC .......... *E04G 23/0214* (2013.01); *A61B 50/33* (2016.02); *B32B 7/12* (2013.01); *B65D 1/34* (2013.01); *E04G 23/0285* (2013.01); *G06K 15/02* (2013.01); *B41J 2/01* (2013.01); *C08G 18/10* (2013.01); *C08G 18/36* (2013.01); *C08G 18/4825* (2013.01); *C08G 18/4829* (2013.01)

(58) Field of Classification Search
None
See application file for complete search history.

(56) References Cited

U.S. PATENT DOCUMENTS

| | | | |
|---|---|---|---|
| 3,507,071 | A | 4/1970 | Bryson |
| 5,677,413 | A | 10/1997 | Barksby et al. |
| 5,864,001 | A | 1/1999 | Masse et al. |
| 6,588,511 | B1 | 7/2003 | Kriesel et al. |
| 6,673,409 | B1 | 1/2004 | Wheatley |
| 6,896,065 | B2 | 5/2005 | Kriesel et al. |

(Continued)

*Primary Examiner* — Jeffrey D Washville
(74) *Attorney, Agent, or Firm* — Bryan R. Rosiejka; M. Paul Hendrickson

(57) ABSTRACT

Hygienic trays adapted to effectively restrain items under hygienic conditions are provided by equipping hygienic trays with an antipathogenic, cohesive and adhesive thermoset overlay provided in the form of an adhesive insert or tray coating. The overlay adhesively restrains emplaced items until manually removed from the overlay by the hygienic user while also providing an unexpected superior antipathogenic environment. The hygienic trays are particularly useful from hygienic applications wherein hygienic conditions and a need to stabilize trayed items against displacement are of a dominant concern. The tray may be of a simple platform design with or without a typical bordering rim which may be adapted for hand carriage or mounted onto another supportive structure.

34 Claims, 4 Drawing Sheets

(56) References Cited

U.S. PATENT DOCUMENTS

| | | | |
|---|---|---|---|
| 7,041,719 | B2 | 5/2006 | Kriesel et al. |
| 7,125,602 | B2 | 10/2006 | Wheatley |
| 7,252,867 | B2 | 8/2007 | Wheatley |
| 7,910,188 | B2 | 3/2011 | Wheatley |
| 7,923,088 | B2 | 4/2011 | Wheatley |
| 8,110,269 | B2 | 2/2012 | Wheatley |
| 8,110,270 | B2 | 2/2012 | Wheatley |
| 8,302,213 | B2 | 11/2012 | Kriesel |
| 9,974,342 | B1 | 5/2018 | Kriesel |
| D880,950 | S | 4/2020 | Kriesel et al. |
| 10,681,830 | B1 | 6/2020 | Goodenough |
| 10,717,582 | B1 * | 7/2020 | Goodenough ....... B65D 81/022 |
| D902,584 | S | 11/2020 | Kriesel et al. |
| D921,401 | S | 6/2021 | Kriesel et al. |
| 2004/0191446 | A1 | 9/2004 | Kriesel |
| 2004/0200623 | A1 | 10/2004 | Kriesel |
| 2006/0272367 | A1 | 12/2006 | Kriesel |
| 2006/0287147 | A1 | 12/2006 | Kriesel |
| 2008/0005929 | A1 | 1/2008 | Hardy et al. |
| 2008/0026658 | A1 | 1/2008 | Kriesel |
| 2008/0250729 | A1 | 10/2008 | Kriesel |
| 2009/0042676 | A1 | 2/2009 | Kriesel |
| 2010/0170139 | A1 | 7/2010 | Zhou |
| 2012/0222457 | A1 | 9/2012 | Kriesel et al. |
| 2013/0142975 | A1 * | 6/2013 | Wallace .................... B32B 7/06 428/36.7 |
| 2013/0288060 | A1 | 10/2013 | Pind et al. |
| 2013/0296449 | A1 | 11/2013 | Peterson et al. |
| 2014/0251866 | A1 * | 9/2014 | Smallman ................ B65D 1/34 206/557 |
| 2015/0053583 | A1 | 2/2015 | McCormick et al. |

\* cited by examiner

STABILIZED HYGIENIC TRAYS

CROSS-REFERENCE TO RELATED APPLICATIONS

This application is a Continuation-in-part of U.S. Non-provisional application Ser. No. 15/731,851 filed Aug. 7, 2017 which is a U.S. Non-provisional Continuation-in-part of application Ser. No. 14/999,722 filed Jun. 20, 2016 which is a non-provisional application of provisional application No. 62/231,004 all of which applications are incorporated in their entirety herein.

FIELD OF INVENTION

The present invention relates to hygienic devices and more particularly to hygienic trays and the use thereof.

BACKGROUND OF THE INVENTION

Medical, dental and other hygienist customarily use hygienic trays for placing hygienic devices, medication, food, etc. and other items in a hygienic, accessible and orderly manner. A common persistent problem arises by an inability to consistently maintain the trayed items in orderly and hygienic condition. Unfortunately many of the needed hygienic supplies are irregular in shape and weight rendering it most difficult to effectively restrain the hygienic items in a presentable hygienic condition and especially under disruptive usage conditions (e.g. dropping, jarring, etc.) which can easily disarrange, damage or contaminate trayed items. Current hygienic trays lack an innate ability to retain trayed items in a hygienic condition until actually needed by the hygienist. Inadvertent dropping, spillage or prolonged stowage of a trayed hygienic item can easily lead to contamination. Current hygienic trays are also environmentally prone to collect pathogens which demands constant attention so as to insure the maintenance of a sterile hygienic environment. A host of restraining systems designed to maintain the hygienic articles in an orderly and hygienic condition have heretofore been proposed.

Examination room hygienic trays are often provided with a stainless steel topside tray in a wheeled or legged cabinet form. Such examination room trays are inherently prone to accumulate pathogens requiring constant attention in order to maintain a sterile environment. Airborne or manually transmitted contaminants deposited upon a tray will remain pathogenically active until subsequently sterilized such as by periodic antibacterial cleansing, autoclaving, etc. Since there often exists a need to use stowed hygienic items and devices before such routine pathogenic sterilization occurs, there persistently exists a high risk of pathogenic infection to the treated patient. To reduce such inadvertent pathogenic contamination hygienic precautions such as the use of surgical marks, gowns and gloves are commonly used to protect against pathogenic contamination. This, however, does not reduce preexisting pathogens already harboring upon a contaminated tray.

It is also common practice to use plastic or metal food trays for hospital, institutional, school, nursing home, restaurant, cafeteria, etc. to feed patients and patrons from a remote food preparation source. There exists a high degree of potential airborne and human pathogenic contamination through food servicing from a remote kitchen. Covering individually the trayed food items with heavy covers, aluminum foil or plastic films are commonly used as protective precautions.

There exists a need for hygienic trays which would effectively restrain hygienic items in an open and orderly hygienic condition while also providing a readily accessible hygienic tray for hygienic use. It would be highly advantageous if there existed a hygienic tray which inherently possessed antipathogenic properties to protect against airborne pathogenic contamination. This would be of particular advantage since such a hygienic tray would offer constant pathogenic protection as opposed to the current practice of a need for persistent pathogenic sterilization safeguards. A hygienic tray which maintained an antipathogenic environment over relatively long periods of time while yet being washable or autoclavable would represent a substantial advance to the hygienic art. The aforementioned benefits may be effectively achieved by coating or inlaying hygienic trays with a unique viscoelastomeric thermoset possessing exceptional cohesive, adhesive and antipathogenic properties. It has been discovered that certain of these viscoelastomeric thermoset coatings or inlays will tenaciously retain an emplaced hygienic item at its stowed position in an effective antipathogenic environment until needed by the hygienist or patron. The current need for continuous sterilization of stowing trays and a fear of jarring or spilling stowed hygienic items becomes of little concern because of the unique antipathogenic cohesive and adhesive properties arising through the use of unique thermoset overlays.

BRIEF SUMMARY OF THE INVENTION

The age old problem of restraining hygienic items in an orderly, stabilized, hygienic and openly accessible hygienic form has been effectively alleviated by overlaying or bonding onto a suitable hygienic supportive member (e.g. a dental, medical, institutional, etc. tray) an adhesive thermoset polymeric overlay possessing antipathogenic properties and sufficient adhesiveness to effectively restrain a host of hygienic items while also allowing for an orderly retrieval of selected hygienic items from the tray by applying an outwardly pulling force sufficient to overcome the adhesive attraction between the hygienic item and the thermoset overlay. The thermoset overlay also possesses sufficient internal cohesiveness so as to cleanly release itself from the removed hygienic item without leaving any visible thermoset residue upon the released hygienic item.

A particularly effective thermoset overlay comprises a thermoset reaction product generally characterized as possessing antipathogenic effectiveness, an adhesive release strength of at least 300 grams force per square centimeter ($gf/cm^2$) and sufficient compositional integrity so as to remain substantially intact after its adhesive separation from the released hygienic item. The most effective thermoset overlays include the antipathogenic thermoset viscoelastomeric polymerizates formulated with a sufficient amount of thermosetting cross-linking and straight chain precursors and plasticizers so as to provide effective antipathogenic properties as well as the desired level of adhesive release strength for hygienic use herein.

The thermoset overlays may be bonded to the topical surface of a tray by adhesively bonding or by thermosetting of an uncured reaction media overlay coating onto the bed of a tray. The thermoset polymerizates applicable herein characteristically possess adhesive thermosetting bonding properties which, if desired, allow a cured thermoset overlay upon in situ thermosetting to become tenaciously bonded to a suitable supportive base. Such a base may comprise either a flexible base or an inflexible or solid supportive base. The cohesive and adhesive characteristics of the overlaying thermoset polymerizate alternatively will permit its use as an adhesive removable overlay adhesively bonded to the supportive base. Although the thermoset overlay has a tendency to adhesively attract dust and other external airborne contaminates resulting in an adhesive loss, the overlay adhesive loss may easily be restored by customary cleansing techniques such as by washing (e.g. manual, or machined) chemical sterilization, autoclaving, etc. If desired, a temporary protective covering may be used to temporarily protect the thermoset against surface dust collection and other contaminates. Unlike conventional hygienic trays, trays provided with the thermoset overlay effectively provide a healthy and antipathogenic environment for stowing of hygienic articles.

BRIEF DESCRIPTIONS OF THE FIGURES

DETAILED DESCRIPTION OF THE INVENTION

Figure 1:
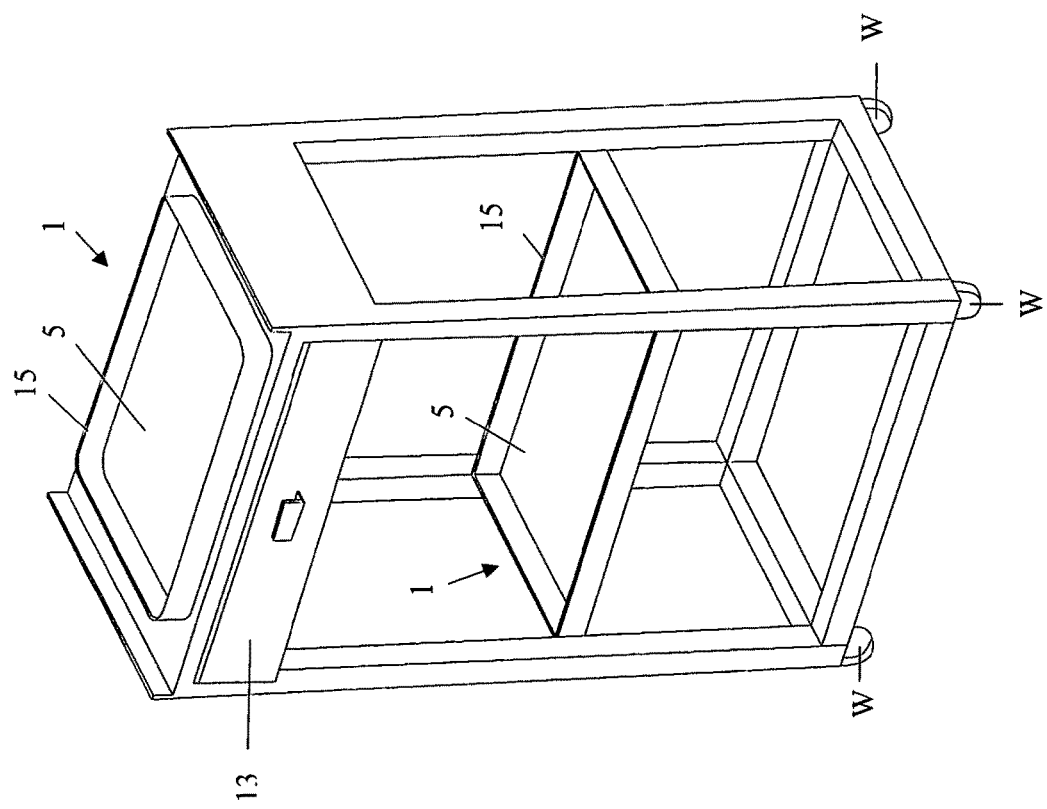
FIG. 1 depicts a perspective view of a wheeled hygienic cabinet equipped with an antipathogenic, adhesive and cohesive thermoset polymerizate overlay bonded to a topside tray.
Figure 2:
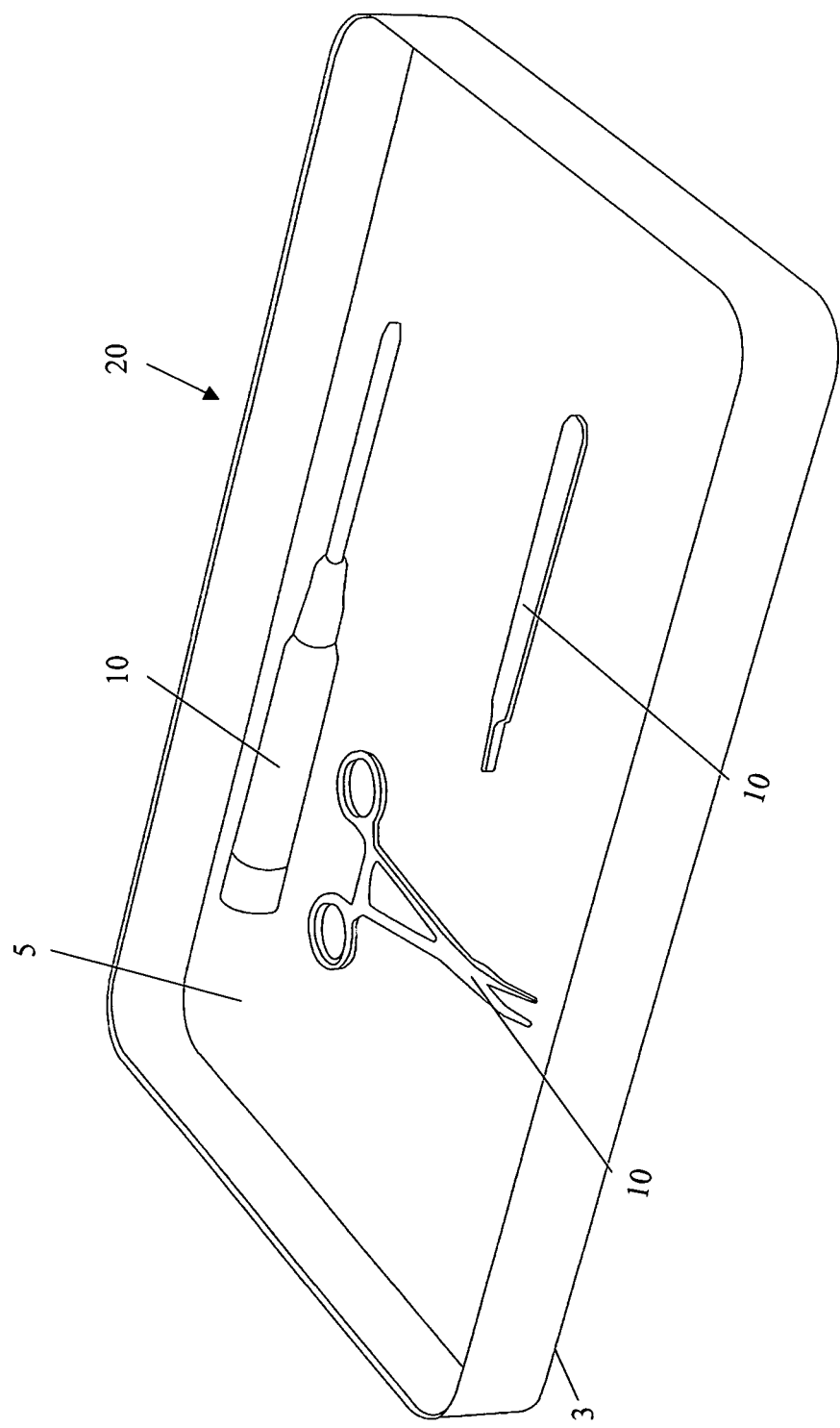
FIG. 2 depicts a perspective view of the upper hygienic tray shown by FIG. 1 with the tray being shown as containing an array of a hygienic items adhesively engaged thereupon.

With reference to FIGS. 1-4, the present invention provides a hygienic tray 1 comprised of a supportive tray base (prefixed by 3) and a viscoelastomeric, cohesive, adhesive and antipathogenic thermoset polymerizate overlay 5 bonded (by physical adhesion or by thermosetting bonding) to the tray base 3. If desired the hygienic tray 1 may be provided as a totable tray combination 20 including multiple trays 1 and suitably equipped with wheels W as shown in FIG. 1 and if desired, be provided in a hand carriable tray form. The basic tray unit 1 may be provided in a cabinet form equipped with drawers 13 and other desired amenities such as side rails 15, handles 17, etc. Since the thermoset overlay 5 effectively adhesively restrains items 10 emplaced thereupon in a steadfast restrained position, conventional compartmentalize tray sections 13 (e.g. drawers), side rails 15, covers 11 or other confining systems are generally unneeded.

The cohesive and adhesive thermoset overlay 5 is generally characterized as having sufficient adhesiveness to adhesively engage and restrain a host of hygienic items 10 at an emplaced stowable position. The restrained items 10 will remain in the original adhesively restrained position until physically removed from the overlay 5. Typically such a removal will be achieved by applying an outward pulling force sufficient to overcome the adhesive attraction between the viscoelastomeric thermoset overlay 5 and the adhered item 10. A suitable test for determining the adhesive efficacy of an overlay 5 may be determined by ascertaining the particular adhesion release strength value for any given adhesive thermoset polymerizate overlay 5. The adhesion release strength testing procedure and testing apparatus for its determination is disclosed in greater detail in our co-pending non-provisional application Ser. No. 15/731,851.

The thermoset polymerizate when used as an overlay 5 should possess sufficient adhesive attraction towards the emplaced hygienic item 10 so as to effectively restrain it at an orderly restrained position. From a user's vantage, an excessively high adhesion release strength value may make it more difficult to remove a hygienic item 10 from the overlay 5. Accordingly as the adhesion release strength values increases, the force needed to remove the hygienic item 10 from the overlay 5 will correspondingly increase. At the higher adhesion release strength values (e.g. 1,200 gf/cm$^2$) it becomes a more strenuous task to remove an adhered item 10. Excessive adhesive attraction forces can make it necessary for the hygienic user to hold onto the tray 1 with one hand while removing the hygienic item 10 therefrom with the other hand. Since it is desirable to provide sufficient tack or adhesiveness to restrain the hygienic item 10 at a restrained orderly position while still making it relatively easy for the hygienic user to remove the item 10 one handedly, the adhesion release strength for most common usage will typically range from about 400 gf/cm$^2$ to about 900 gf/cm$^2$.

The overlays 5 generally useful herein include certain thermoset polymerizate meeting the necessary antipathogenic properties and adhesion release strength values coupled with an innate ability to cohesively retain structural integrity upon its separation from the hygienic item 10 without leaving more than a miniscule amount of polymerizate residue upon the separated item 10.

The thermoset overlays 5 may be effectively bonded to the hygienic tray bed 3B by physically adhesively bonding a prefabricated overlay 5 to the tray bed 3B by simply relying upon the adhesiveness of the thermoset polymerizate overlay 5 for the bonding. Alternatively by curing a thermosetting reaction product precursor (i.e. thermosetting reaction media) of the viscoelastomeric thermoset upon the tray bed 3B, the resultant in situ thermoset polymerizate overlay 5 becomes more firmly bonded thereto.

The overlays 5 may be suitably prepared from a thermosetting reaction media tailored to provide the desired antipathogenic, cohesive and adhesive thermoset attributes which renders it particularly adapted for use as an overlay 5. A particular effective reaction media for preparing the antipathogenic, cohesive and adhesive overlay 5 herein involves providing a thermosetting reaction media containing from about 25% to less than 52% by weight plasticizer characterized as having an epoxidized triglyceride plasticizer content of less than 50%, from about 35% by weight to about 55% by weight of straight chain linking diols and cross-linking polyols and from about 4% to 7% by weight of a polyurethane precursor (e.g. a polyol reacted with an isocyanate). The content and the type of the linking polyols have been found to have pronounced effect upon imparting the necessary thermoset polymeric infrastructure for preparing the desired unique cohesive and adhesive viscoelastomeric thermoset overlay 5 attributes herein. An appropriate balance between straight chain producing diols and cross-linking polyols (e.g. triol) provides an effective reaction media for preparing a polyurethane reaction product (i.e. thermoset viscoelastomer) possessing especially unique antipathogenic, cohesive and adhesive compositional properties for use as a stabilizing adhesive overlay 5 herein. A reaction product overlay 5 having an adhesion strength of less than 300 grams force per square centimeter (gf/cm$^2$) will generally fail to provide a sufficient adhesive strength to restrain the hygienic item 10 in a stabilized and stowable form. Adhesiveness of the stabilizing overlay 5 necessarily depends upon a proper polyol balance within the thermosetting reaction media. It has been found that when the weight ratio of diols to triols in the presence of an effective amount of plasticizer within the reaction media falls outside a weight ratio of about 7:13 to about 13:7, the resultant reaction media will generally fail to provide a desired stabilizing thermoset viscoelastomer having an adhesion release strength of more than 300 grams of force per square centimeter.

An effective thermoset viscoelastomeric polymerizate overlay 5 will characteristically possesses a capacity to adhesively restrain the hygienic item 10 at a desired stabilized position upon an appropriate supportive base 3 while also allowing for an effective release of the hygienic item 10 therefrom upon an application of an outwardly counteracting force sufficient to overcome the adhesive force attraction between the hygienic item 10 to the overlay 5. The thermoset overlay 5 also possesses a tenacious internal compositional cohesiveness as evidenced by its ability to break cleanly away from its adhesive bonding to the hygienic item 10. Characteristically upon adhesive separation, the overlay 5 will return to its substantially intact and innate form with no more than a minuscule level of stabilizing overlay 5 adhering to the separated hygienic item 10. Upon separation there will accordingly exist no evidence of visible overlay residue remaining upon the separated hygienic item 10 after separation from the overlay 5 with the overlay 5 readily returning to its innate form.

The plasticized cross-linked polymeric structure of the thermoset polymerizate obtained from an appropriate thermoset reaction media balance provides an ideal infrastructure for effectively harboring plasticizing components in an unexpectedly superior cohesive and adhesive form while also contributing the highly desired and effective antipathogenic properties to the overlay 5. The plasticizer is uniformly incorporated into the thermosetting reaction media containing the polymerizable thermosetting components and remains uniformly dispersed within the resultant thermoset reaction product in a highly adhesive and stabilized antipathogenic form. Typically the amount of plasticizer within the reaction media will range from about 20% to about 55% by weight of the total reaction media weight with the plasticizer being uniformly dispersed throughout the reaction media and the resultant thermoset viscoelastomer derived therefrom. Most appropriately the thermosetting reaction media used in providing the most effective overlays 5 will contain from about 20% to about 48% by weight plasticizer. The plasticizer content will typically constitute from 0% to about 48% by weight of a triglyceride plasticizer (e.g. an epoxidized triglyceride) and from about 0% to about 40% by weight of an ester plasticizer more typically as a di-ester plasticizer. The thermosetting diols and triols in cooperative combination with the plasticizer create an antipathogenic environment as well as a thermoset viscoelastomeric polymeric structure possessing the high degree of compositional adhesiveness necessary to adhesively secure and retain the hygienic item 10 to the overlay 5 while also allowing for a clean cohesive separation from the hygienic item 10. Thus, the type of plasticizer and reactants in monitored amounts can be effectively utilized to provide desirable thermosetting fabricating conditions as well as the ultimate reaction product and an overlay 5 possessing the desired unique beneficial attributes.

The diol may be typically provided by a polyetherdiol having a molecular weight ranging from about 2,000 to about 6,000 in an amount ranging from about 10% to about 20% by weight of the reaction media weight. The diol provides sufficient cross-linkage disruption and straight chain infrastructure formation to permit a highly effective loading of the viscoelastomeric thermoset with the antipathogenic, cohesive and adhesive plasticizer co-factor. The cross-linking triol content suitably provided a polyethertriol (typically of a molecular weight ranging from about 3,000 to about 7,000) will most suitable range from about 25% to about 35% by weight of the reaction media weight. The reaction media also suitably includes a conventional polyurethane precursor typically in amount from about 4% to about 7% by weight (e.g. di-isocyanate prepolymer) and from about 20% to about 48% by weight plasticizer bound within the thermoset reaction infrastructure suitably formulated to provide a thermoset viscoelastomeric reaction product overlay having an adhesion release strength of at least 400 grams force per centimeter square ($gf/cm^2$).

Although the antipathogenic viscoelastomeric thermoset overlay 5 will generally possess unexpectedly superior adhesiveness, the thermoset overlay 5 will also possesses unexpectedly superior releasable cohesive attributes. Upon exposure to a separating adhesive release force (e.g. such as pulling the hygienic item 10 away from it adhesive engagement), the compositional adhesiveness of the viscoelastomeric thermoset overlay 5 tenaciously retain its structural integrity by separating cleanly from the hygienic item 10 without leaving more than a trace compositional residue upon the separated hygienic item 10. As the overlay tack level increases, there arises a cohesive and adhesive tendency of the overlay 5 to pull away from the adhesively engaged hygienic item 10 in a taffy-like manner until the stabilizing overlay 5 completely separates or breaks cleanly away from the adhered hygienic item 10. However the stretched portion of the overlay 5 tends to readily cohesively return to its innate overlay 5 form. The overall tackiness and adhesiveness of the viscoelastomeric thermoset stabilizing overlay 5 and its concomitant releasability characteristics may be altered by the compositional makeup of the thermosetting reaction media, particularly by the diol to triol reaction media ratio as well as the reaction media plasticizer content and type of plasticizer. Thus, the cohesive and adhesive attributes of the thermoset viscoelastomeric stabilizing overlay 5 may be tailored to meet the desired level of adhesiveness for hygienic use. An effective manner for regulating the adhesion release strength of the thermoset overlay 5 involves altering the diol to triol reactant ratio of the thermosetting reaction media. In general, the adhesion release strength (i.e. more tacky) will decrease as the triol reactant content increases and increase when the diol content increases. In order to compensate for a diol reaction media increase, a slight increase in the di-isocyanate reactant amount will generally serve to balance the reaction media reactants. Surprisingly the cohesiveness of the stabilizing overlay 5 is maintained throughout an adhesion release strength range of at least 300 $gf/cm^2$ to 900 $gf/cm^2$. Typically the higher the adhesion release strength values will tend to cause the overlay 5 to tenaciously string out similar to the pulling of heated candy taffy until a clean adhesive separation ultimately occurs whereupon the overlay 5 cohesively returns to its innate form. The high tack levels make it more difficult for the hygienic user to effectively release the hygienic item 10 from the stabilizing overlay 5 and especially at an adhesion release strength levels of more than 900 $gf/cm^2$. For general hygienic use, it is typically desirable for the overlay 5 to provide a secure adhesive bonding while allowing for an ease of one handed hygienic item 10 (e.g. adhesion release strength of about 400 to about 900 $gf/cm^2$)

retrieval which becomes more difficult at the more elevated adhesion release strength levels.

The viscoelastomeric stabilizing overlay 5 may be provided in a performed insert overlay form. In this form, the preformed insertable overlay 5 may be bonded by adhesively inserting the adhesive inlay 5 onto a tray bed 3B or whatever other tray position the overlay 5 is desirably needed. Due to the exceptional adhesive and cohesive qualities of the viscoelastomeric thermoset, the overlay 5 may be provided in a film, sheet, strip, insert etc. form which due to its tack will tenaciously adhesively adhere to conventional hygienic tray beds 3B until a counteracting force causes its removal. Alternatively the thermosetting reaction media for forming the overlay 5 may be directly bonded in situ to the tray bed 3B by applying a flowable thermosetting reaction media of the thermosetting reactants to the bed 3 and thereafter allowing the reaction media to cure in situ to provide a thermoset viscoelastomeric overlay 5 bonded by thermosetting to the bed 3.

Irrespective of how the overlay 5 is bonded to the hygienic tray 3, the viscosity characteristics of uncured thermosetting reaction media of the cured polymerizate may be effectively tailored so as to provide a workable viscosity for effectively fabricating the thermoset overlay 5 into its desired form. The thermosetting reaction media for preparing the thermoset viscoelastomer overlay 5 may accordingly be characteristically formulated so as to possess the desired film forming, coating, and molding properties during its initial formative thermosetting stages. Conventional calendaring, casting, molding, coating, etc. thermosetting film forming techniques may be effectively used to prepare the overlay 5 in either a coated thermoset or insertable form at a workable viscosity range. The viscosity of the thermosetting reaction media may be suitably formulated so as provide sufficient fluidity to allow for the tray coatings, filming or other molding processes such as normally utilized under conventional thermoset molding, casting, and etc. techniques. The lower viscosity stages of the viscoelastomeric thermosetting reaction are generally best suited for the overly prefabrication. Procedurally a measured amount of the viscous but sufficient fluid thermosetting reaction media may be deposited or casted upon a hygienic tray bed 3B in a desired amount allowed to spread evenly (due to a desirable casting viscosities) and then cured in situ to provide the desired overlaying member 5 tenaciously bonded to the tray bed 3B. Controlling the initial viscosity properties of the thermosetting reaction media accordingly provides a convenient manufacturing procedure for fabricating a hygienic tray 1 equipped with an effective thermoset stabilizing overlay 5 bonded thereto.

By effectively adjusting the plasticizer content and type, the characteristics of the reaction media including the ultimate thermoset tack as well as the initial thermosetting reaction media viscosity characteristics, the thermosetting reaction media may be tailored so as to suit a particular type of manufacture. For example, an effective casted coating manufacture procedurally typically requires a workable viscosity so that the desired coating or film may be produced. This generally entails pouring, injecting, casting, etc. of the thermosetting reaction media at workable viscosity onto a supportive substance (e.g. tray surface) to provide a uniformly casted coating, film, sheet, etc. to form the desired overlay 5. Particularly suitable for such fabricating purposes involves formulating the reaction media with an effective amount of viscosity reducing di-ester plasticizers and especially the di-alkyl esters of di-carboxylic acids. These di-ester plasticizers generally impart sufficient onset fluidity reduction so as to provide a thermosetting reaction media which may be easily poured, molded or casted during its initial thermosetting stages. Characteristically these di-alkyl ester plasticizers are fluid at room temperature (e.g. 20° C.) and have a molecular weight of less than 500. Exemplary thereof are the condensation products of alcohols (e.g. the $C_1$ to $C_{10}$ alcohols) and the $C_2$-$C_{12}$ dicarboxylic acids and particularly the condensates of a $C_4$-$C_8$ dicarboxylic acids and the $C_2$ to $C_6$ alcohols.

Typically the total plasticizer concentration will most suitably range from about 20% to about 45% by weight of the reaction media weight and most typically ranges from about 25% to about 40% by weight. The weight ratio of epoxidized triglyceride to non-epoxidized plasticizer (e.g. di-esters) within the reacting media will typically range from about 1:0 to about 1:3 and most typically from about 1:1 to about 3:1 and especially under those thermosetting conditions wherein the di-ester plasticizers are used to prepare the stabilizing overlay 5.

Since it is desirable for most manufacturing applications to use a more fluid thermosetting reaction media, those di-ester plasticizers normally fluid at room temperatures are particularly effective for this purpose. The enhanced fluidity characteristic imparted to the thermosetting reaction media by the di-esters becomes particularly useful in conventional casting procedures such as the casting of thin film or the casting of coatings upon the hygienic tray bed 3B. Such thermosetting casting techniques also tend to create a more tenacious bonding between the cured stabilizing overlay 5 and the tray bed 3B than adhesive bonding. Amongst the more fluid di-ester plasticizers are the lower di-alkyl esters of di-carboxylic acids. Exemplary thereof are the di-alkyl esters having alkyl groupings of less than 12 carbon atoms and more typically of the $C_1$ to $C_8$ di-alkyl ester grouping of sebecates, the adipates, the isophthalates, the phathalates, the maleates, and the azelates, the gluterates, etc. The total plasticizer concentration in such casting manufacturing technique will most suitably range from about 20% to about 45% by weight and most typically range from about 25% to about 40% by weight with the weight ratio of epoxidized triglyceride to non-epoxidized plasticizer (e.g. di-esters) typically ranging from about 1:0 to about 1:3 and most typically from about 1:1 to about 3:1. Due to the availability, excellent reaction media viscosity for fabricating and end product characteristics, dibutyl sebecate has been found to be a highly effective di-alkyl ester plasticizer. A balanced proportion of triglyceride and di-alkyl ester plasticizers (e.g. about 1:1 to about 1:0) has generally been found to provide useful attributes in providing a desired thermosetting viscosity and reaction product (i.e. stabilizing overlay 5). On a reaction media weight basis, the di-alkyl ester plasticizer content for casting purposes will desirably range from about 1% to about 20% by weight and most typically from about 5% to about 15% by weight of the total reaction media weight.

When effectively used as a stabilizing overlay 5 bonded to the hygienic tray bed 3B, the overlay 5 will restrain the hygienic item 10 at a desirable preset position. The hygienic item 10 will steadfastly maintain its emplaced position without incurring any undesirable movement notwithstanding exposure to relatively powerful disruptive external forces. Consequently abruptly dropping or jarring the hygienic tray combination 20 stocked with stowed items 10 will typically fail to dislodge the stowed item 10 from their restrained mooring to the stabilizing overlay 5. In contrast to conventional hygienic trays which are notoriously known for a propensity to scatter trayed hygienic items 10 when abruptly dislodged, the hygienic tray combination 20 as provided by this invention will tenaciously restrain a seated hygienic item 10 to its original emplaced seating under the most rigorous abusive conditions. Thus, an abrupt movement of the hygienic combination 20 equipped with the stabilizing overlay 5 will still restrain and protect the stowed item 10 from dislodgement. These exceptional stabilizing effects are accomplished while still providing an ease or removal and emplacement of the stowed item within the hygienic tray combination 20.

Figure 3:
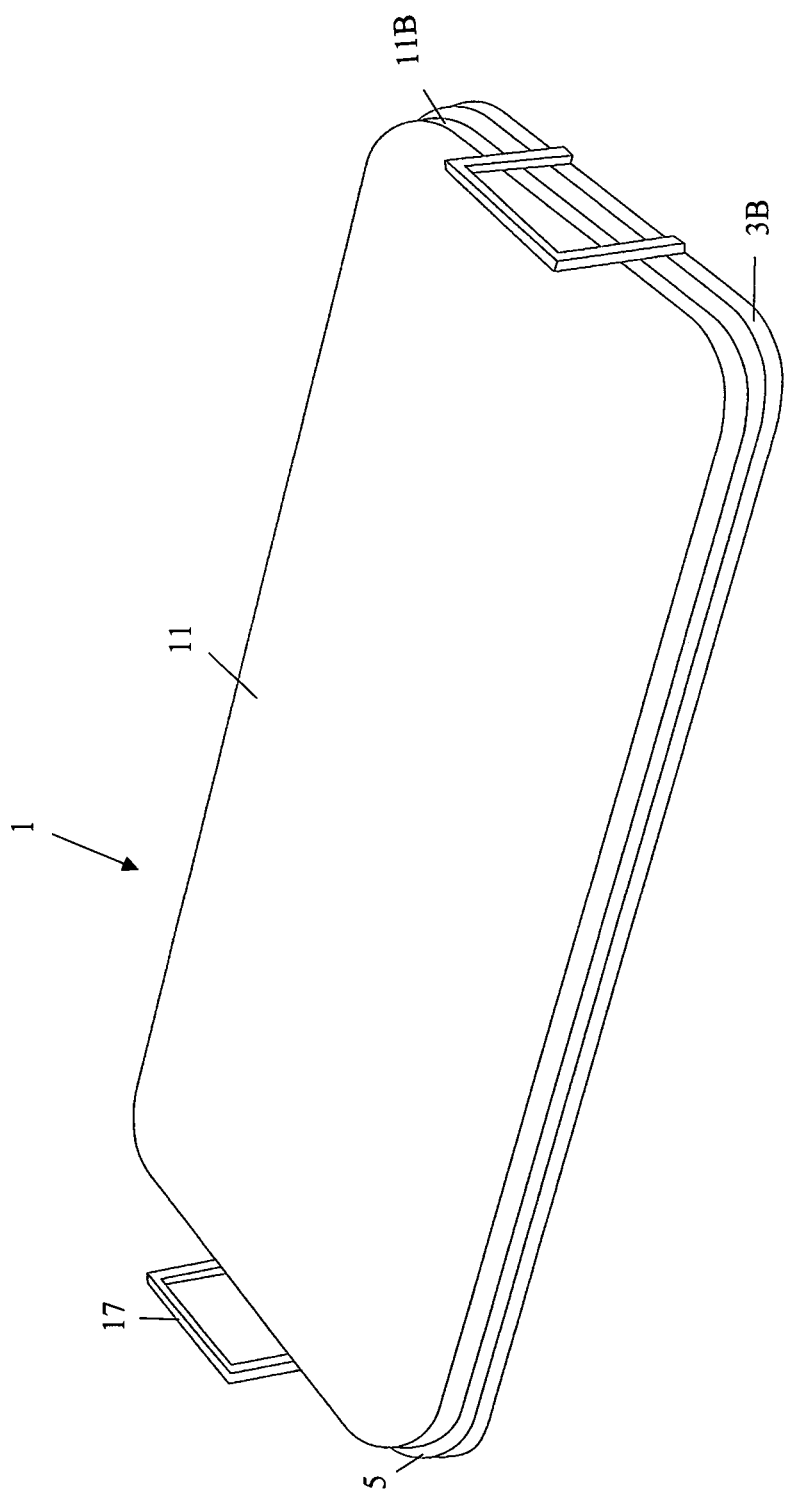
FIG. 3 depicts an elevated view of a transparent hygienic tray equipped with an adhesively entrained covering protective lid and carrying handles.
Figure 4:
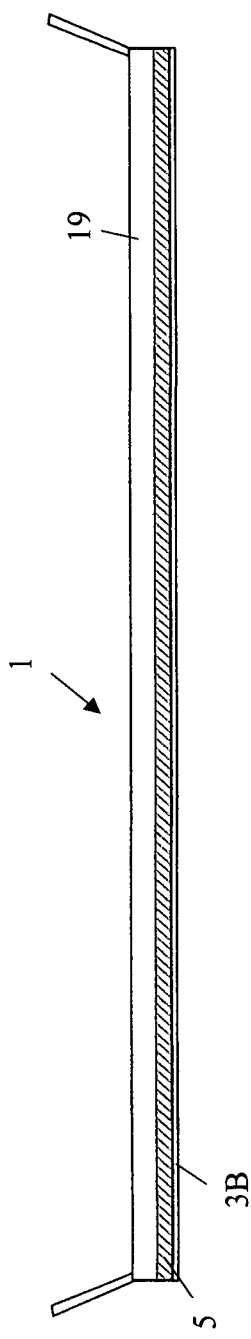
FIG. 4 is a cross-sectional view of the FIG. 3 hygienic tray without the covering lid.

The stabilized hygienic tray 1 may be conveniently provided with other tray amenities such as a removable covering lid 11 as depicted by FIG. 3. The covering lid 11 may be designed to be easily removable from its adhered lid position so as to permit ease of tray access. The covering lid 11 may be hinged but preferably provided in the detachable or otherwise removable from its covering positions. The covering lid 11 may be completely removable from the tray 1 which relying upon its interfacing relationship with the overlay 5 to adhesively restrain the lid 11 in its covering position until overtly removed. This feature is particularly unique because the overlay 5 provides an adhesive, cohesive and hygienic environment for retaining the covering lid 11 in a tenacious bond to the overlay 5 which in turn is hygienically bonded to the hygienic tray 1 support. The advantage to this adhesive and hygienic bonding is readily apparent for those hygienic applications requiring hygienic covering of potentially pathogenic harboring stowed items until ultimately used. For example it is customary practice to individually fit reusable hospital, cafeteria and institutional food trays with loosely held covering lids which are highly susceptible to dislodgement by jarring or dropping. The ability to provide a covered hygienic tray combination 20 with a cohesive, adhesive and antipathogenic tray overlay 5 (e.g. covering a whole or part of the tray bed 3B) and an adhesively restrained removable lid cover 11 represents a unique hygienic advantage over conventional use of food trays. If desired, but not necessary a centered peripheral rim 19 for the tray covering may be provided to assist in proper lid 11 placement. The overlay 5 creates the desired hygienic cohesive and adhesive bonding of the removable covering lid 11 to the tray 1 without needing any other vertical support.

The use of the hygienic adhesive and cohesive thermoset overlay 5 applies broadly to its usefulness as a hygienic tray overlay including its combination with a tray accessory such as the removable covering lid 11 mentioned above having the thermoset overlay 5 seated to the brim 11B of covering lid 11 or to the bed surface 3B of the tray 1. The overlay 5 may also be utilized to prevent tray slippage or dislodgement from a solid surface such as a hospital bed table. To accomplish this objective, the underside of the hygienic tray 1 may include a bonded overlay 5 adapted to maintain the hygienic tray 1 in a fixed position once the tray 1 is placed at a desired position of use. Thus the hygienic tray 1 may provide an effective means of stabilizing the tray 1 as well as the stowed items 10 thereupon against unwanted dislodgement. Another effective use of the hygienic trays 1 includes a cafeteria style tray which are notoriously recognized as being highly prone to inadvertent frayed food spillage if not maintained in a stable and level hand carried position. The adhesive tack of the thermoset overlay 5 serves to adhesively adhere to the frayed items 10 so as to prevent spillage, dropping, overturning, etc. of the adhesively restrained trayed items 10.

The overlay 5 need not completely cover the hygienic tray 1 but may effectively be utilized to partially cover a sufficient area of the tray surface so as to adhesively secure a desired hygienic item 10 thereto. Thus the overlay 5 may accordingly be bound to the tray surface in a continuous, discontinuous or irregular overlay form. Overlaying striations and spaced positioning inclusive of virtually any geometric configuration of sufficient surface area coverage to adhere and stabilize the desired hygienic item 10 to be stowed thereupon may be effectively used as an overlay 5. Thus if it is desired to maintain a domed shaped covering lid 11 in a stable position, the overlay 5 may be overlaid onto the tray surface to mate onto covering lid 11 so as to thereby adhere and maintain the covering lid 11 securely attached relationship to the hygienic tray 1. Similarly the topographical tray surface may be partially or completely coated to match the covering lid rim.

The hygienic tray 1 may be constructed of any supportive substrate which provides a sufficient supportive base 3 for the thermoset overlay 5. Since the overlay 5 possesses excellent viscoelastomeric properties it may be used as an overlay 5 for both flexible and solid tray supports. Illustrative flexible supports 3 may include those adapted to be folded and opened in a tray form such as paramedic bags. Solid substrates such as those of metal (e.g. stainless steel, tin, aluminum, etc.) plastic (thermoset of thermoplastics) or any other suitable solid support may effectively be utilized to provide a solid tray support 3. The hygienic tray embodiments of this invention broadly apply to a broad spectrum of general purpose hygienic trays fitted with the cohesive, adhesive and antipathogenic overlay 5. The trays 1 are particular adaptable to the health care trays 1 (e.g. medical, dental, optical, hospital, assisted living, nursing homes, chiropractic, personal health care, emergency, health care uses, etc.) as well as for hygienic food tray usage (e.g. institutional, cafeteria, food packaging, etc.). Since the overlay 5 adhesively restrains items 20, the trays 1 as provided by this inventions may be equipped or not equipped with conventional raised rims. The "tray" definition herein accordingly broadly applies to a substantially flat supportive structure (e.g. platform with or without a raised rim or recessed structure) of sufficient size to provide the desired support of the adhesive base or overlay 5. The tray 1 may accordingly constitute a bed section of a drawer 13 equipped with the adhesive overlay 5.

Example

A thermosetting reaction media possessing excellent casting viscosity characteristics and suitably formulated to serve as a casted overlay 5 upon a conventional hygienic tray bed 3B was prepared from a uniform admixture of the following mix of thermosetting reactants:

| | Percent by Weight: |
|---|---|
| A-Mix Ingredients: | |
| Methylene diphenyl diisocyanate based glycol prepolymer (ElastoCAST TQZP23 by BASF Corporation) | 6.46% |
| Epoxidized soybean oil | 26.88% |
| Dibutyl sebecate | 8.96% |
| B-Mix Ingredients: | |
| Polyurethane precursor mix formulated polyether triol (ElastoCAST C-4057 by BASF Corporation) | 26.88% |

-continued

| | Percent by Weight: |
|---|---|
| Polyether diol (ElastoCAST C-4018 by BASF Corporation) | 29.32% |
| Catalyst (COSCAT 83) | 0.16% |
| Tinuvin B75 (UV inhibitor) | 1.30% |
| Dye Blend (1:1) | 0.05% |
| Total | 100% |

During the initial thermosetting stages, a bed 3B comprised of a conventional high density polypropylene hygienic tray 1 was uniformly coated with a 100 mil thick coating of the aforementioned reaction media by casting measured coating amounts of the uniform admixture onto the hygienic tray bed 3B. The container bed 3B had been preflamed to permit a more effective bonding of the stabilizing overlay 5 thereto. The casted thermosetting overlay coating was allowed to fully cure to provide a thermoset viscoelastomer stabilizing overlay 5 characterized as having an average adhesion release strength of 800 (average derived from 10 tested samples).

The resultant hygienic tray was suitably adapted to receive a host of hygienic stowable items 10 such as medical scissors, digital pulse and oxygen sensors, clips, bandages, tongue depressors, thermometers, clamps, forceps, scalpel, etc. Similarly hygienic food trays for health care and institutional use may be suitable prepared with the thermoset overlay 5. Notwithstanding strenuous abusive mishandling, the emplaced hygienic items 13 were able to maintain their original placement position upon the bed overlay 5. The adhesion release strength value of casted overlay 5 permitted the hygienic user to easily one handedly remove a desired hygienic item 10 from the overlay 5.

The efficacy of an antipathogen is customarily assessed by using known pathogens which are generally recognized as pathogenic test standards. In order to assess the antipathogenic properties of the overlay 5, an antifungal assessment test (A.A.T.C.C Test method 30-2004) inoculated with *Aspergillus niger* (ATCC #6275) was conducted upon smooth and rough surfaced overlay test samples which test results registered a zero (0) score as being fungal growth as free for both the smooth side and a rough side test samples. The overlay surface inhibition of fungal growth measured in terms of antifungal percent inhabitation of *Aspergillus niger* growth was 100% inhibition which is indicative of the highly effective antifungal attributes of the overlay 5.

In order to test the antibacterial efficacy of thermoset overlay against microbial growth, test samples of the overlay 5 were subjected to AATCC Test method 147-2004 using *Staphylococcus aureus* ATCC #6538 as a standard microbial inoculant. The tested inoculated thermoset overlay samples included both rough side and smooth side testing. Similar to the antifungal test results, the bacterial tests resulted in both test sides indicating a zero (0) growth free zone. The testing revealed a 100% inhabitation against Staph growth also for both the smooth and roughened side test samples. The aforementioned tests represent standardized antipathogenic tests as commonly used by the industry to establish the antipathogenic efficacy. Common to some of the known antipathogenic agents, the thermoset overlay 5 substantially retards pathogenic growth by retarding pathogenic growth by a factor of more than a 50% inhabitation of pathogenic growth. As may be surprisingly observed from the aforementioned test results, the thermoset overlay 5 provides an antipathogenic surface environment substantially free pathogenic growth. The antipathogenic growth may accordingly be effectively limited to nominal (e.g. miniscule) growth factor for hygienic trays 1 containing the thermoset overlay 5 of this invention. The highly effective antipathogenic attributes coupled with its unique cohesive and adhesive properties, herein create a highly versatile thermoset overlay 5 for hygienic tray applications.

Hygienic tray 1
Supportive Base 3
Overlay 5
Tray Bed 3B
Handle 9
Stowed Items 10
Top lid/cover 11
Lid brim 11B
Drawer 13
Rails 15
Handles 17
Rim 19
Hygienic combination 20
Wheels W

What is claimed is:

1. A hygienic tray equipped to restrain an emplaced item at a stabilizing stowable position until manually removed therefrom, wherein the hygienic tray comprises a supportive base having an antipathogenic, cohesive and adhesive thermoset viscoelastomeric overlay bonded to the supportive base.

2. The hygienic tray according to claim 1 wherein the thermoset overlay is prepared by a thermosetting a reaction media comprising a substantially uniform admixture of an isocyanate precursor, an effective amount of plasticizer containing less than 50 percent by weight of an epoxidized triglyceride plasticizer, from about 35 to about 55 percent by weight polyols, wherein the polyols consist essentially of a straight chain linking diol and a cross-linking polyol each of which contain repetitive oxy groups, and wherein the reaction media further comprises a diol to polyol weight ratio ranging from about 1:2 to about 2:1.

3. The hygienic tray according to claim 2 wherein the supportive base comprises a tray bed equipped with a removable lid bonded to the overlay.

4. The hygienic tray according to claim 2 wherein the overlay has an adhesion release strength ranging from about 400 to about 900 gf/cm$^2$.

5. The hygienic tray according to claim 2 wherein the overlay comprises an overlaying thermoset coating obtained by thermosetting an overlaying coating of the reaction media.

6. The hygienic tray according to claim 1 wherein the supportive base comprises a hygienic exam room table having the overlay bonded to a topside surface of the exam room table.

7. The hygienic tray according to claim 2 wherein the supportive base comprises a tray bed and the overlay comprises a viscoelastomeric thermoset coating bonded to the tray bed by thermosetting a coating of the reaction media thereto.

8. The hygienic tray according to claim 7 wherein the tray includes a plurality of stowed items adhesively engaged to the overlay.

9. The hygienic tray according to claim 1 wherein a thermosetting reaction media for preparing the thermoset overlay comprises:
  a. about 4% to 7% by weight di-isocyanate prepolymer;
  b. about 25% to about 35% by weight polyether triol as a cross-linking polyol;

c. about 10% to about 35% by weight polyether diol as a straight chain producing polyol; and d. about 20% to 55% by weight plasticizer uniformly dispersed within the reaction media;

wherein the reaction media further comprises a diol to triol weight ratio of about 7:13 to about 13:7; and wherein the plasticizer comprises less than 50% by weight epoxidized triglyceride plasticizer and about 0% to about 40% by weight di-ester plasticizer.

10. The hygienic tray according to claim 9 wherein the epoxidized triglyceride plasticizer comprises about 35% to about 48% by weight of the total reaction media weight and wherein the diol to triol weight ratio ranges from about 2:3 to about 3:2.

11. The hygienic tray according to claim 9 wherein the plasticizer comprises about 25% to about 50% by weight di-ester plasticizer.

12. The hygienic tray according to claim 11 wherein the di-ester plasticizer comprises dibutyl sebacate and a thermoset coating of the reaction media provides the overlay.

13. The hygienic tray according to claim 11 wherein the polyether triol comprises a polyoxyalkylene having a molecular weight of about 3,000 to about 7,000 and is selected from the group consisting of polyoxyethylene triol and polyoxypropylene triol.

14. The hygienic tray according to claim 13 wherein the polyether diol has a molecular weight of about 2,000 to about 6,000 and is selected from the group consisting of polyoxyethylene diol and polyoxypropylene diol.

15. The hygienic tray according to claim 14 wherein the supportive base comprises a tray bed equipped with a movable covering lid bonded to the overlay.

16. The hygienic tray according to claim 14 wherein the tray includes a wheeled undercarriage.

17. The hygienic tray according to claim 16 wherein the tray comprises adhesively restrained items bonded to the overlay.

18. The hygienic tray according to claim 14 wherein the tray comprises a medical tray.

19. The hygienic tray according to claim 18 wherein the overlay comprises a detachable adhesive overlaying insert adhesively affixed to a topside surface of the medical tray.

20. The hygienic tray according to claim 18 wherein the overlay comprises a thermoset viscoelastomeric coating bonded to a topside surface of the medical tray.

21. A method for manufacturing a hygienic platform adapted to retard pathogenic growth and restrain a stowed item in contact therewith, said method comprising:

a. providing a hygienic supportive base comprising a supportive platform;

b. preparing an antipathogenic, cohesive and adhesive thermoset viscoelastomeric overlay having an adhesive capacity to cleanly release from the stowed item without leaving more than minuscule amount of overlay residue upon release therefrom; and c. applying the overlay or a thermosetting precursor of the overlay to the supportive platform to provide the antipathogenic, cohesive and adhesive viscoelastomeric overlay possessing sufficient adhesiveness to releasably restrain the stowed item.

22. The method according to claim 21 wherein the preparing of the overlay comprises uniformly admixing together a thermosetting reaction media comprising:

a. about 4% to 7% by weight di-isocyanate prepolymer;

b. about 10% to 35% by weight polyether diol c. about 25% to about 35% by weight polyether triol; and d. a sufficient amount of plasticizer;

wherein the reaction media further comprises a diol to triol weight ratio of about 7:13 to about 13:7.

23. A hygienic tray combination having a supportive base supportive of hygienic items emplaced thereupon, comprising an antipathogenic cohesive and adhesive thermoset viscoelastomeric overlay disposed upon the supportive base and having sufficient adhesiveness to restrain the emplaced items at a desired stabilized position while also allowing for a release of the emplaced items from the overlay by applying a sufficient counteracting force to separate the emplaced items from the overlay, wherein the overlay cohesively separates from the hygienic items without leaving more than trace amounts of the overlay upon the items separated therefrom while the overlay remains firmly bonded to the supportive base upon the separation of the hygienic items therefrom.

24. The hygienic tray combination according to claim 23 wherein the overlay consists essentially of a thermoset viscoelastomeric polymerizate.

25. The hygienic tray combination according to claim 24 wherein the overlay comprises an adhesion release strength ranging from at least 300 gf/cm$^2$ to about 800 gf/cm$^2$.

26. The hygienic tray combination according to claim 25 wherein the supportive base comprises a solid tray bed, and wherein the overlay has an outer exposed adhesive surface for interfacial adhesive engagement onto the emplaced items.

27. The hygienic tray combination according to claim 26 wherein the hygienic tray combination comprises a food tray equipped with a removable covering lid bonded to the overlay.

28. A method of retrofitting a conventional hygienic tray so as to possess antipathogenic, cohesive and adhesive properties, said method comprising:

a. providing an antipathogenic, cohesive and adhesive viscoelastomeric overlay for bonding onto a supportive bed of the conventional hygienic tray; and b. bonding the overlay to the supportive bed so as to provide an antipathogenic, cohesive and adhesive overlay sized to adhesively restrain a desired item emplaced thereupon.

29. The method according to claim 28 wherein the overlay comprises a thermoset viscoelastomeric polymerizate.

30. The method according to claim 29 wherein the providing includes protectively covering the overlay with a protective thermoplastic film to protect the overlay from external contamination, a subsequent removing of the protective thermoplastic film from the overlay followed by an inserting of the overlay onto the supportive bed.

31. The method according to claim 29 wherein the thermoset viscoelastomeric polymerizate consists essentially of a thermoset reaction product of a reaction media comprising:

a. about 4% to 7% by weight di-isocyanate prepolymer;

b. about 10% to about 35% by weight polyether diol;

c. about 25% to about 35% by weight polyether triol; and d. a sufficient amount of plasticizer;

wherein the reaction media further comprises a diol to triol weight ratio of about 7:13 to about 13:7.

32. The method according to claim 31 wherein the polyether diol comprises a member selected from the group consisting of polyoxyethylene diol and polyoxypropylene diol and having molecular weight of about 2,000 to about 6,000, and wherein the polyether triol comprises a member selected from the group consisting of polyoxyethylene triol and polyoxypropylene triol and having a molecular weight of about 3,000 to about 7,000.

33. The method according to claim 32 comprising a diol to triol weight ratio of 2:3 to 3:2.

34. The method according to claim 33 comprising an adhesion release strength of about 400 gf/cm$^2$ to about 700 gf/cm$^2$.

\* \* \* \* \*